(12) United States Patent
Hahl et al.

(10) Patent No.: US 11,450,486 B2
(45) Date of Patent: Sep. 20, 2022

(54) ELECTROLYTIC CAPACITOR HAVING A TANTALUM ANODE

(71) Applicant: Greatbatch Ltd., Clarence, NY (US)

(72) Inventors: Jason T. Hahl, East Aurora, NY (US); Christina Scheuer, Amherst, NY (US); Barry C. Muffoletto, Alden, NY (US); Anthony C. Perez, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 17/221,444

(22) Filed: Apr. 2, 2021

(65) Prior Publication Data

US 2021/0313118 A1 Oct. 7, 2021

Related U.S. Application Data

(60) Provisional application No. 63/004,532, filed on Apr. 3, 2020.

(51) Int. Cl.
| | |
|---|---|
| *H01G 9/052* | (2006.01) |
| *H01G 9/08* | (2006.01) |
| *A61N 1/378* | (2006.01) |
| *H01G 9/035* | (2006.01) |
| *H01G 9/042* | (2006.01) |

(52) U.S. Cl.
CPC .......... *H01G 9/0525* (2013.01); *H01G 9/08* (2013.01); *A61N 1/378* (2013.01); *H01G 9/035* (2013.01); *H01G 9/0425* (2013.01)

(58) Field of Classification Search
CPC ............................ H01G 9/0525; H01G 9/08
See application file for complete search history.

(56) References Cited

U.S. PATENT DOCUMENTS

| | | | | |
|---|---|---|---|---|
| 4,544,403 A | * | 10/1985 | Schiele ................ | H01G 9/0525 420/427 |
| 4,645,533 A | * | 2/1987 | Izumi ........................ | B22F 9/24 420/427 |
| 4,940,490 A | * | 7/1990 | Fife ....................... | B22F 1/0055 75/229 |
| 5,369,547 A | | 11/1994 | Evans et al. | |

(Continued)

FOREIGN PATENT DOCUMENTS

| | | |
|---|---|---|
| CN | 1308566 A | 8/2001 |
| WO | 0067936 A1 | 11/2000 |

*Primary Examiner* — Eric W Thomas
(74) *Attorney, Agent, or Firm* — Michael F. Scalise

(57) ABSTRACT

A wet tantalum electrolytic capacitor containing a cathode, fluidic working electrolyte, and anode formed from an anodically oxidized sintered porous tantalum pellet is provided. The pellet is formed from a pressed tantalum powder. The tantalum powder is formed by reacting a tantalum oxide compound, for example, tantalum pentoxide, with a reducing agent that contains a metal having an oxidation state of 2 or more, for example, magnesium. The resulting tantalum powder is nodular or angular and has a specific charge that ranges from about 11,000 μF*V/g to about 14,000 μF*V/g. Using this powder, wet tantalum electrolytic capacitors have breakdown voltages that ranges from about 250 volts to about 400 volts. This makes the electrolytic capacitors ideal for use in an implantable medical device.

22 Claims, 7 Drawing Sheets

(56) References Cited

U.S. PATENT DOCUMENTS

| | | | |
|---|---|---|---|
| 5,448,447 A * | 9/1995 | Chang | C22C 1/045 |
| | | | 361/529 |
| 5,894,403 A | 4/1999 | Shah et al. | |
| 5,920,455 A | 7/1999 | Shah et al. | |
| 6,197,252 B1 | 3/2001 | Bishop et al. | |
| 6,219,222 B1 | 4/2001 | Shah et al. | |
| 6,224,985 B1 | 5/2001 | Shah et al. | |
| 6,231,993 B1 | 5/2001 | Stephenson et al. | |
| 6,468,605 B2 | 10/2002 | Shah et al. | |
| 6,594,140 B1 | 7/2003 | Evans et al. | |
| 6,687,117 B2 | 2/2004 | Liu et al. | |
| 6,819,544 B1 * | 11/2004 | Nielsen | H01G 9/042 |
| | | | 361/508 |
| 6,850,405 B1 * | 2/2005 | Mileham | H01G 9/26 |
| | | | 361/302 |
| 7,012,799 B2 | 3/2006 | Muffoletto et al. | |
| 7,092,242 B1 | 8/2006 | Gloss et al. | |
| 7,116,547 B2 | 10/2006 | Seitz et al. | |
| 7,271,994 B2 | 9/2007 | Stemen et al. | |
| 7,431,751 B2 | 10/2008 | Shekhter et al. | |
| 7,483,260 B2 | 1/2009 | Ziarniak et al. | |
| 9,721,730 B1 | 8/2017 | Muffoletto et al. | |
| 9,824,829 B1 | 11/2017 | Muffoletto et al. | |
| 9,875,855 B2 | 1/2018 | Perez et al. | |
| 9,978,528 B2 | 5/2018 | Hahl et al. | |
| 10,020,127 B1 | 7/2018 | Muffoletto | |
| 10,290,430 B2 | 5/2019 | Djebara et al. | |
| RE47,435 E | 6/2019 | Shah et al. | |
| 2003/0110890 A1 | 6/2003 | He et al. | |
| 2004/0163491 A1 | 8/2004 | Shekhter et al. | |
| 2016/0141110 A1 * | 5/2016 | Djebara | H01G 9/08 |
| | | | 607/119 |
| 2018/0137989 A1 * | 5/2018 | Petrzilek | A61N 1/3981 |
| 2019/0172654 A1 * | 6/2019 | Weaver | A61N 1/05 |
| 2019/0272958 A1 * | 9/2019 | Sungail | H01G 11/00 |
| 2019/0272959 A1 | 9/2019 | Perez et al. | |

* cited by examiner

ELECTROLYTIC CAPACITOR HAVING A TANTALUM ANODE

CROSS-REFERENCE TO RELATED APPLICATION

This application claims priority to U.S. provisional patent application Ser. No. 63/004,532, filed on Apr. 3, 2020.

BACKGROUND OF THE INVENTION

1. Field of the Invention

High voltage electrolytic capacitors are often employed in implantable medical devices. However, because it is desirable to minimize the overall size of the implanted device, capacitors that are suitable for high voltage implantable applications are required to have a relatively high energy density. This is particularly the case for an implantable cardioverter defibrillator ("ICD"), also referred to as an implantable defibrillator, because the high voltage capacitors used to deliver the defibrillation pulse can occupy as much as one third of the ICD volume. ICDs typically use two to four electrolytic capacitors in series to achieve the desired high voltage for shock delivery.

One commonly used high voltage capacitor is referred to as a wet tantalum electrolytic capacitor. A wet tantalum capacitor has an anode of a porous sintered tantalum pellet. For example, a tantalum pellet may be formed by compressing a tantalum powder under high pressure followed by sintering at high temperature to form a sponge-like structure, which is very strong and dense but also highly porous. Because of the high voltages encountered in medical devices, however, relatively low specific charge tantalum powders must be employed. Namely, if the specific charge is too high, relatively thin sinter necks tend to form between adjacent particles, which can cause the dielectric layer at and adjacent to the sinter necks to fail at high voltages.

2. Prior Art

U.S. Pat. No. 10,290,430 to Djebara et al. relates to a tantalum material for use as an anode in a wet tantalum electrolytic capacitor. The tantalum powder has a specific charge that ranges from about 15,000 µF*V/g to about 45,000 µF*V/g, which results in a capacitor that can operate at a voltage that ranges from about 100 volts to about 300 volts. This patent further describes that the tantalum material has larger sinter necks that result in higher charge voltages.

However, to further improve the energy density of an electrolytic capacitor for use in an implantable medical device, a need currently exists for an improved tantalum powder with a lower specific capacitance than the tantalum material described in the '430 patent. The resulting improved electrolytic capacitor is intended for use in an implantable medical device, such as an implantable defibrillator.

SUMMARY OF THE INVENTION

In accordance with one embodiment of the present invention, a wet tantalum electrolytic capacitor is disclosed that comprises an anode, a cathode, and a fluidic working electrolyte in contact with the anode and the cathode. The anode comprises an anodically oxidized tantalum pellet formed from a pressed and sintered tantalum powder. The tantalum powder is formed by reacting an oxide of a tantalum compound with a reducing agent that contains a metal having an oxidation state of 2 or more. The cathode comprises a metal substrate coated with a pseudocapacitive coating, preferably of ruthenium oxide coating.

In accordance with another embodiment of the present invention, a wet tantalum electrolytic capacitor is disclosed that comprises an anode, a cathode, and a fluidic working electrolyte in contact with the anode and cathode. The anode comprises an anodically oxidized tantalum pellet formed from a pressed and sintered tantalum powder. The tantalum powder is nodular or angular and has a specific charge that ranges from about 11,000 µF*V/g to about 14,000 µF*V/g. The cathode comprises a metal substrate coated with a pseudocapacitive coating, preferably of ruthenium oxide coating.

In accordance with yet another embodiment of the present invention, a method for forming a wet tantalum electrolytic capacitor is disclosed that comprises pressing a tantalum powder into a pellet. The tantalum powder is formed by reacting tantalum pentoxide with a reducing agent that contains magnesium, calcium, strontium, barium, cesium, aluminum, or a combination thereof, sintering the pellet, anodically oxidizing the sintered pellet to form a dielectric layer that overlies the tantalum powder, and positioning the anode in electrical association with a cathode through contact with a fluidic working electrolyte in a casing.

These and other aspects of the present invention will become more apparent to those skilled in the art by reference to the following description and to the appended drawings.

DETAILED DESCRIPTION OF REPRESENTATIVE EMBODIMENTS

Figure 1:
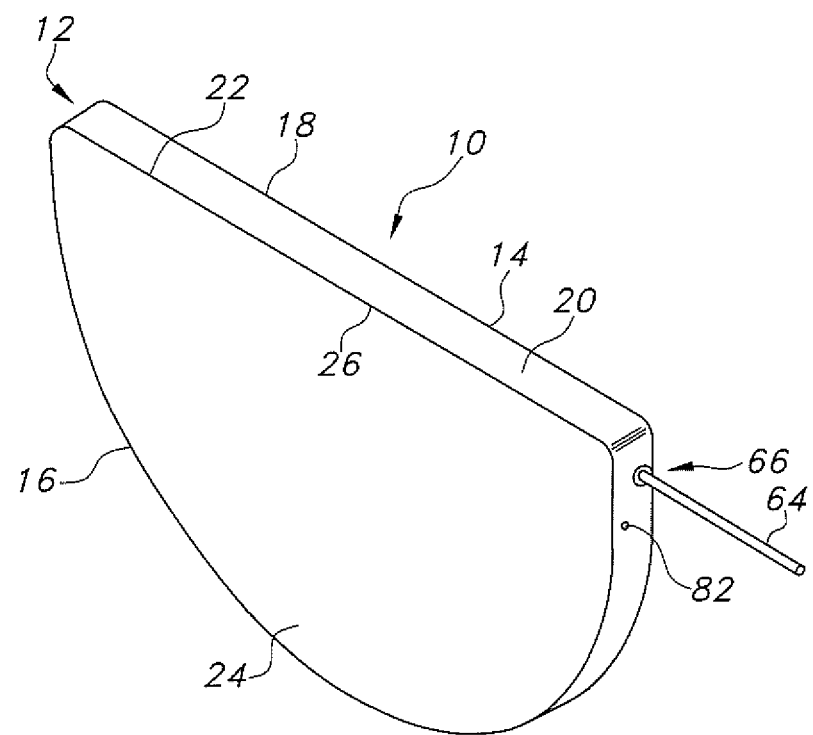
FIG. 1 is a perspective view of an exemplary capacitor 10 according to the present invention.

FIG. 1 is a perspective view of an exemplary wet tantalum electrolytic capacitor 10 according to the present invention. The capacitor 10 comprises at least one tantalum anode and a cathode of a cathode material housed inside a hermetically sealed casing 12. The illustrated casing 12 is exemplary of any one of a myriad of shapes for a capacitor, limited only by the device that the capacitor 10 is designed to be used in. The tantalum anode and the cathode housed inside the casing 12 are in electrical association with each other by a working electrolyte (not shown) contained therein. The anode or anodes, cathode, and working electrolyte of the capacitor 10 will be described in detail hereinafter.

The exemplary casing 12 shown in FIG. 1 has a first drawn casing member 14 closed by a lid 16. The casing members 14, 16 are preferably selected from the group of titanium, tantalum, nickel, molybdenum, niobium, cobalt, stainless steel, tungsten, platinum, palladium, silver, copper, chromium, vanadium, aluminum, zirconium, hafnium, zinc, iron, and mixtures and alloys thereof. In addition to being of a drawn form, casing member 14 can be of a machined construction or be formed by a metal injection molding process. Preferably, the casing members have a thickness of about 0.001 inches to about 0.015 inches.

The first casing member 14 has a first face wall 18 joined to a surrounding side wall 20 extending to an edge 22. The second casing member 16 has the shape of a plate with a second face wall 24 having a surrounding edge 26. The casing members 14 and 16 are hermetically sealed together by welding the overlapping or abutting edges 22 and 26 where they contact each other. The weld is preferably provided by laser welding.

Figure 2:
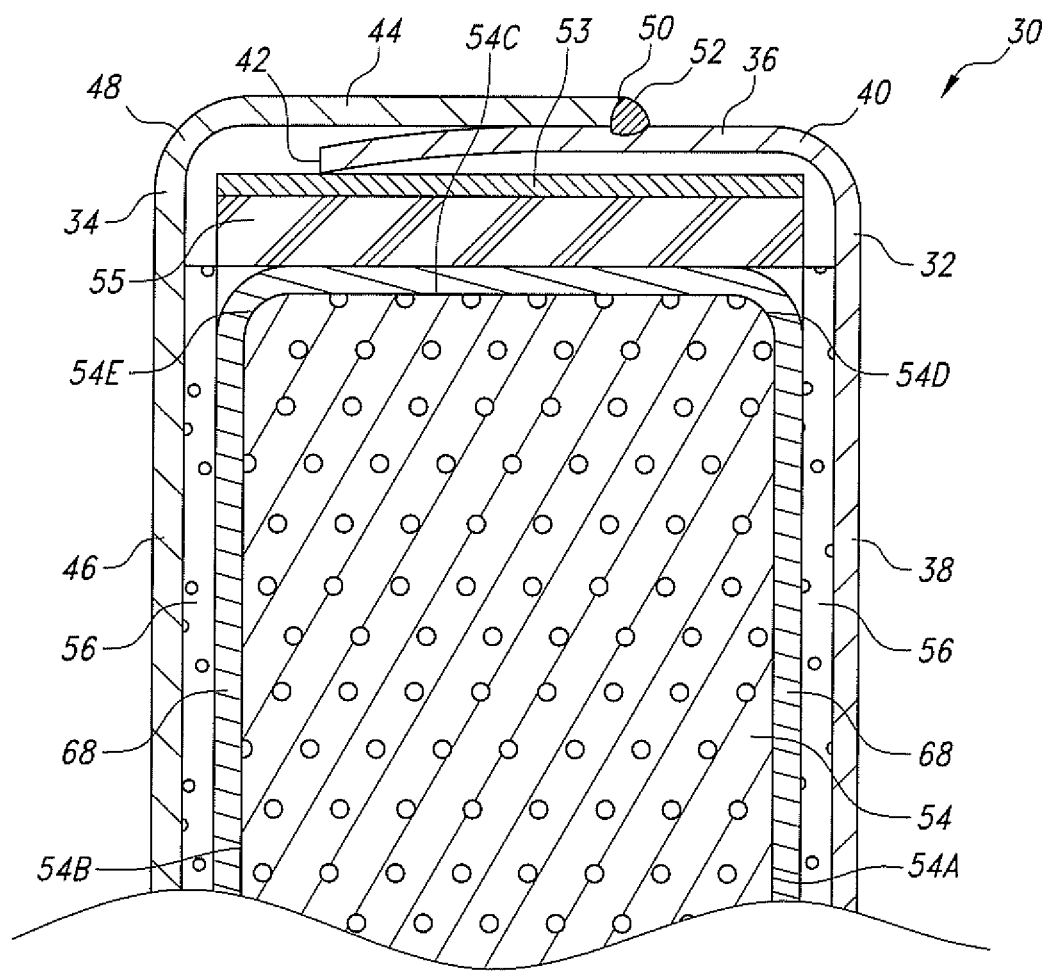
FIG. 2 is a partial cross-sectional view of the capacitor 10 shown in FIG. 1 but comprising a casing 30 of mating clamshell-type members 38, 46 housing a single anode 54 operatively associated with a cathode 56 supported on the inner surfaces of the casing members.

FIG. 2 illustrates another embodiment of an exemplary casing 30 according to the present invention. The exemplary casing 30 has mating drawn clamshell-type member 32 and 34. The first clamshell-type casing member 32 comprises a surrounding sidewall 36 extending to and meeting with a major face wall 38 at a curved intermediate bend 40. Opposite bend 40, the surrounding sidewall 36 extends to a continuous, perimeter edge 42. Similarly, the second clamshell-type casing member 34 comprises a surrounding sidewall 44 extending to and meeting with a major face wall 46 at a curved intermediate bend 48. Opposite bend 48, the surrounding sidewall 44 extends to a continuous perimeter edge 50. However, face wall 38 is somewhat smaller than face wall 46 so that its surrounding sidewall 36 fits inside the surrounding sidewall 44 of the second casing member 34 in an overlapping, contact relationship. That way, casing 30 is hermetically sealed by providing a weld 52 at the surrounding sidewall 36 of the first casing member 32 and the edge 50 of the second casing member 34.

Other casing structures that are useful with the present capacitor 10 are described in U.S. Pat. No. 7,012,799 to Muffoletto et al., U.S. Pat. No. 7,092,242 to Gloss et al., U.S. Pat. No. 7,271,994 to Stemen et al., U.S. Pat. No. 9,978,528 to Hahl et al., U.S. Pat. No. 9,721,730 to Muffoletto et al., U.S. Pat. No. 9,824,829 to Muffoletto et al., U.S. Pat. No. 9,875,855 to Perez et al. and U.S. Pat. No. 10,020,127 to Muffoletto, all of which are assigned to the assignee of the present invention and incorporated herein by reference.

As shown in FIG. 2, a weld strap 53 is provided directly adjacent to the surrounding sidewall 36 of casing member 32. The weld strap 53 is an annular, ring-shaped member surrounding the anode end wall 54C and is typically of the same metal as that of the casing members 32, 46. An intermediate polymeric insulating ring 55 seats against the weld strap 53 and a separator 68 portion covering the anode end wall 54C. The weld strap 53 in conjunction with the insulating ring 55 help shield the separator 68 at the anode end wall 54C from the heat generated as the casing members 32, 46 are welded together.

The single anode 54 housed inside the exemplary casing 30 illustrated in FIG. 2 is of tantalum. As is well known by those skilled in the art, the anode metal in powdered form, for example tantalum powder, is compressed into a pellet of a desired shape. In the illustrated embodiment, the anode pellet is of a substantially uniform thickness extending to spaced apart right and left major sidewalls 54A, 54B joined by an end wall 54C. The major sidewalls 54A, 54B meet the intermediate wall 54C at respective curved edges 54D, 54E. The curved edges 54D, 54E are of a substantially similar radius as that of the casing bends 40, 48, respectively.

The cathode material 56 preferably coats the inner surfaces of the major face walls 38, 46 of the respective casing members 32, 34 in a pattern that generally mirrors the shape of the right and left major sidewalls 54A, 54B of the anode 54. The cathode material 56 preferably has a thickness of about a few hundred Angstroms to about 0.1 millimeters and is either directly coated on the inner surfaces of the face walls 38, 46 or it is coated on a conductive substrate (not shown) supported on and in electrical contact with the inner surfaces thereof. The cathode material coatings are preferably spaced from the surrounding sidewalls 36, 44 of the respective casing members 32, 34.

In that respect, the major face walls 38, 46 of the casing members 32, 34 may be of an anodized-etched conductive material, have a sintered active material with or without oxide contacted thereto, be contacted with a double layer capacitive material, for example a finely divided carbonaceous material such as graphite, carbon, platinum black, a redox, pseudocapacitive, or an under potential material, or be an electroactive conducting polymer such as polyaniline, polypyrrole, polythiophene, polyacetylene, and mixtures thereof.

According to one preferred aspect of the present invention, the redox or cathode material 56 includes an oxide of a metal, a nitride of the metal, a carbon nitride of the metal, and/or a carbide of the metal, the oxide, nitride, carbon nitride and carbide having pseudocapacitive properties. The metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead. In a preferred embodiment of the present invention, the cathode material 56 includes an oxide of ruthenium or oxides of ruthenium and tantalum.

A pad printing process as described in U.S. Pat. No. 7,116,547 to Seitz et al. is preferred for providing such a coating. An ultrasonically generated aerosol as described in U.S. Pat. Nos. 5,894,403, 5,920,455, 6,224,985, and 6,468,605, all to Shah et al., is also a suitable deposition method. These patents are assigned to the assignee of the present invention and incorporated herein by reference.

Figure 3:
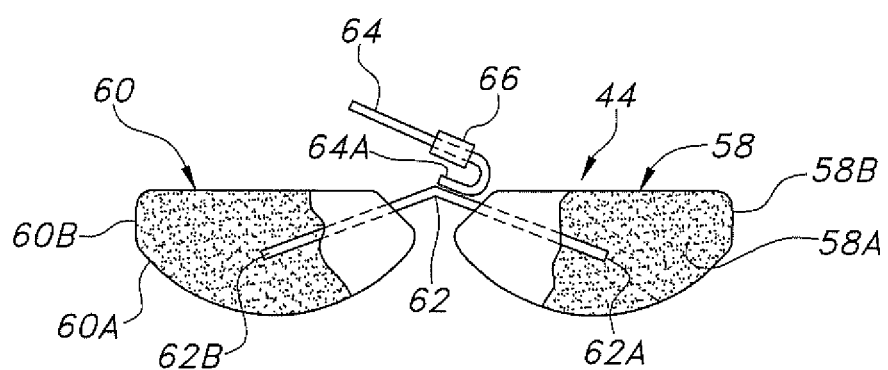
FIG. 3 is a side elevation view of an anode assembly comprising a pair of anodes 58 and 60 connected in parallel to the anode terminal wire 64 of a feedthrough 66.

In contrast to the single anode embodiment shown in the exemplary capacitor of FIGS. 1 and 2, FIG. 3 is a side elevation view of an anode assembly for the capacitor 10 of FIG. 1 where the anode assembly including a first anode 58 and a second anode 60. For the sake of clarity of illustration, the anode assembly is depicted prior to bending the connecting wire so that the faces of the anodes 58 and 60 are positioned near or adjacent to each other with a cathode current collector supporting a cathode material disposed there between.

The first anode 58 comprises an outer major face wall 58A opposite an inner major face wall (not numbered), both face walls extending to a surrounding edge 58B. Similarly, the second anode 60 comprises an outer major face wall 60A opposite an inner major face wall (not numbered), both face walls extending to a surrounding edge 60B. A connecting wire 62 has a first portion 62A embedded in the first anode 58 and a second portion 62B embedded in the second anode 60. The connecting wire 62 is a continuous member that is electrically connected to the J-shaped interior portion 64A of an anode terminal wire 64 of a hermetic feedthrough 66 by a suitable joining process, such as laser welding. This means that the first anode 58 and the second anode 60 are connected to the terminal wire 64 in parallel. Alternatively, the first wire portion 62A and the second wire portion 62B are separate wires (not shown) that are joined to the J-shaped portion 64A of the terminal wire 64.

While the casing 12 shown in FIG. 1 is described as housing a dual anode system 58 and 60 and the mating clamshell-type casing 30 shown in FIG. 2 is described as housing a single anode 54, it is within the scope of the present invention that either casing 12 or 30 can house a single anode, two anodes, or more than two anodes. If more than two anodes, for example "n" anodes, there will be n−1 cathode current collectors supporting a cathode material positioned between immediately adjacent anodes.

Figure 4:
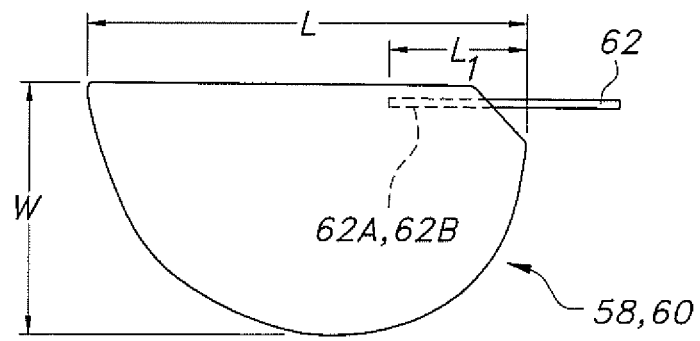
FIG. 4 is a side elevational view of the anodes 58 and 60 shown in FIG. 3 for use in the capacitor 10 shown in FIG. 1.

As shown in FIG. 4, in an exemplary embodiment, the length "L" of the tantalum anodes 54 (FIG. 2) and 58 and 60 (FIG. 3) ranges from about 1 to about 80 millimeters, more particularly from about 10 to about 60 millimeters, and still more particularly from about 20 to about 50 millimeters. Likewise, the length "$L_1$" that the wires 62A, 62B are embedded in the tantalum anode 54, 58 and 60 preferably ranges from about 1 to about 40 millimeters, in some embodiments, from about 2 to about 20 millimeters, and in some embodiments, from about 5 to about 15 millimeters. The width "W" of the tantalum anodes 54, 58 and 60 is preferably from about 0.05 to about 40 millimeters, in some embodiments, from about 0.5 to about 35 millimeters, and in some embodiments, from about 2 to about 25 millimeters.

Figure 5:
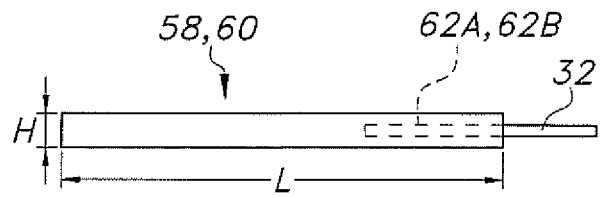
FIG. 5 is a plan view of the top edge of the anodes 58 and 60 shown in FIG. 4.

To improve the electrical performance and volumetric efficiency of the capacitor 10, the thickness of the anodes 54, 58 and 60 is relatively thin. For example, the thickness of the anodes 54, 58 and 60 represented by the dimension "H" in FIG. 5 is about 5 millimeters or less, more particularly from about 0.05 to about 4 millimeters, and still more particularly from about 0.1 to about 3.5 millimeters. The ratio of the length of the anode to its thickness is from about 5 to about 50, more particularly from about 6 to about 30, and still more particularly from about 7 to about 20. Although shown having a "D-shape" in FIGS. 3 to 5, the anodes 54, 58 and 60 may have any desired shape, such as square, rectangle, circle, oval, triangle, and the like.

In that respect, the anodes 54, 58 and 60 are individually formed from an anodically oxidized sintered porous valve metal pellet, preferably a tantalum powder pellet. Preferably, each anode pellet is made from a pressed tantalum powder, which is formed by reacting a tantalum oxide, for example, tantalum pentoxide, with a reducing agent that contains a metal having a relatively high oxidation state, for example, an oxidation state of 2 or more. Exemplary metals for the reducing agent include alkaline earth metals, for example, magnesium, calcium, strontium, barium, cesium, aluminum, and the like. Through use of such tantalum powder, an electrolytic capacitor exhibiting relatively high capacitance is achieved, which is advantageous when the intended use of the capacitor 10 is for use in an implantable medical device. The tantalum powder is preferably a tantalum oxide that is capable of being reduced, such as $Ta_2O_x$ ($x \leq 5$), for example, $Ta_2O_5$.

The reducing agent is provided in a gaseous, liquid, or solid state, and may be in the form of the metal, as well as alloys or salts thereof. In one embodiment, a halide salt, for example, a chloride or fluoride is used. If desired, other components may be added before, during, or after the reduction reaction, such as dopants, alkali metals, and the like.

Reduction of the tantalum oxide is typically carried out at a temperature that ranges from about 400° C. to about 1,200° C., and in some embodiments from about 600° C. to about 1,000° C., for about 20 to about 300 minutes. Heating may be carried out in a reactor under an inert atmosphere, for example, an argon or nitrogen atmosphere so that a molten bath is formed. Suitable reactors include vertical tube furnaces, rotary kilns, fluid bed furnaces, multiple hearth furnaces, self-propagation high-temperature synthesis reactors, and the like. Preferably the reactor is maintained under an inert gas until the mass in the reaction vessel is cooled to ambient temperature. Additional details of such a reduction reaction are described in U.S. Pub. Nos. 2003/0110890 to He et al. and 2004/0163491 to Shekhter et al.

After the reduction reaction, the tantalum powder is cooled, crushed, and washed to remove excess impurities or reactants. The washing solution may include, for example, a mineral acid and water. If desired, the tantalum powder may be subjected to additional treatment to remove any tantalates, for example, magnesium tantalate that may have formed during the reduction reaction. For example, one technique for removing tantalates involves heating the tantalum powder under vacuum at a temperature that ranges from about 1,100° C. to about 1,400° C. for about 15 minutes to about 6 hours. Another technique for removing tantalates involves heating the tantalum powder at a temperature that ranges from about 800° C. to about 1,300° C. in the presence of a getter material, such as magnesium, calcium and/or aluminum, for about 15 minutes to about 6 hours. Such techniques are described in more detail in U.S. Pat. No. 7,431,751 to Shekhter et al. Although not required, the resulting tantalum powder may be subjected to additional refining steps as is known in the art, such as doping, deoxidizing, and the like.

Regardless the method used, the resulting tantalum powder is a free-flowing, finely divided powder that contains primary particles having a three-dimensional shape, such as a nodular or angular shape. Such particles are not generally flat and thus have a relatively low "aspect ratio", which is defined as the average diameter or width of the particles divided by the average thickness ("D/T"). For example, the aspect ratio of the tantalum particles may be about 4 or less, in other embodiments about 3 or less, and in still other embodiments from about 1 to about 2.

The tantalum powder also has a relatively high specific surface area, such as about 0.5 square meter per gram ("$m^2/g$") or more, in other embodiments about 2 $m^2/g$ or more. The term "specific surface area" generally refers to surface area as determined by the physical gas adsorption (B.E.T.) method described by Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from Quantachrome Corporation, Syosset, N.Y., which measures the quantity of adsorbate nitrogen gas adsorbed on a solid surface by sensing the change in thermal conductivity of a flowing mixture of adsorbate and inert carrier gas, for example, helium.

Due to its relatively high surface area and low particle size, the tantalum powder of the present invention has a high specific charge that ranges from about 11,000 to 14,000 microFarads*Volts per gram ("μF*V/g"). As is known in the art, the specific charge is determined by multiplying capacitance by the anodizing voltage employed, and then dividing this product by the weight of the anodized tantalum body. Despite the use of such high specific charge tantalum powders with three-dimensional particles, the reduction process described above is believed to result in "sinter necks" between adjacent agglomerated particles that are relatively large. Sinter necks are the small cross-sectional area of the electrical path within the metal structure. Typically, the sinter necks have a size of about 200 nanometers, or more, in some embodiments about 250 nanometers, or more, and in some embodiments, from about 300 to about 800 nanometers. Because the sinter necks are relatively large, the dielectric layer near the neck is more likely not to fail at high forming voltages.

The tantalum powder (as well as the exemplary anodes 54, 58 and 60 formed from the powder) has a relatively low alkali metal, carbon, and oxygen content. For example, the tantalum powder has no more than about 50 ppm carbon or alkali metals, and in some embodiments, no more than about 10 ppm carbon or alkali metals. More particularly, two batches of tantalum powder received from H. C. Starck, now Taniobis GmbH, were analyzed. The qualitative results are listed below.

| Tantalum Powder Lots | | |
|---|---|---|
| Characteristic | Lot A | Lot B |
| H | 22 | 33 |
| N | 293 | 261 |
| O | 1456 | 1255 |
| Mg | 7 | 7 |
| C | 32 | 32 |
| Fe | <3 | <3 |
| Cr | <2 | <2 |
| Ni | <3 | <3 |
| Si | <3 | <3 |
| P | 21 | 21 |
| Apparent density, Scott (cube) g/cm$^3$ | 1.8 | 2.1 |
| Flow time 0.15 inch/Vib.40/25 g (sec) | 20 | 16 |
| Specific surface TriStar m$^2$/g | 0.5 | 0.6 |
| Pellet Weight (mg) | 150 | 150 |
| Pellet Shape | Cylindrical | Cylindrical |
| Pellet Length (mm) | 3.8 | 3.7 |
| Pellet Diameter (mm) | 3.0 | 3.0 |
| Pellet Density (g/cm$^3$) | 5.4 | 5.4 |
| Sintering Temperature (° C.) | 1500 | 1560 |
| Sintering Time (min) | 20 | 20 |
| Shrinkage, Volume (%) | 10.7 | 11.6 |
| Formation Voltage (V) | 300 | 300 |
| Formation Condition H3PO4/Glycol (uS/cm) | 350 | 350 |
| Formation Temperature (° C.) | 60 | 60 |
| Capacitance @ 120 Hz (µFV/g) | 12940 | 12052 |
| Leakage Current (nA/µFV) | 1.9 | 2.4 |

To facilitate construction of the anodes 54, 58 and 60, additional materials may be included in the tantalum powder. For example, the tantalum powder may be mixed with a binder and/or a lubricant to ensure that the particles adequately adhere to each other when compacted or pressed to form a pellet. Suitable binders include, for example, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene; polyethylene; polyethylene glycol (e.g., Carbowax from Dow Chemical Co.); polystyrene, poly(butadiene/styrene); polyamides; polyimides; and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly(lower alkyl methacrylates) and copolymers of lower alkyl acrylates and methacrylates; and fatty acids and waxes, such as stearic and other soapy fatty acids, vegetable wax, micro-waxes (purified paraffins), and the like.

The binder may be dissolved or dispersed in a lubricating solvent. Exemplary solvents include water, alcohols, and the like. When utilized, the percentage of binder and/or lubricant may range from about 0.1% to about 8% by weight of the total mass. It should be understood, however, that a binder and a lubricant is not necessarily required to form the exemplary anodes 54, 58 and 60 for use in the capacitor 10.

To form an anode, the resulting tantalum powder is compacted into a pellet using any conventional powder press device. For example, a press mold may be employed that is a single station compaction press containing a die and one or multiple punches. Alternatively, an anvil-type compaction press mold that uses only a die and single lower punch may be used. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. As previously shown in FIG. 3, the tantalum powder may be compacted around the connecting wire 62, 62A and 62B that is formed from any electrically conductive material, such as tantalum, niobium, aluminum, hafnium, titanium, and the like, as well as electrically conductive oxides and/or nitrides thereof. Preferably, a tantalum connecting wire 62 is used with a tantalum powder pellet.

If a binder or lubricating solvent is used, the binder or lubricant is removed after pressing by heating the pellet under vacuum at a temperature that ranges from about 150° C. to about 500° C. for several minutes. Alternatively, the binder/lubricant is removed by contacting the tantalum pellet with an aqueous solution, such as described in U.S. Pat. No. 6,197,252 to Bishop et al.

The tantalum pellet is then sintered to form a porous, integral mass. Sintering typically occurs at a temperature that ranges from about 800° C. to about 2,000° C., more particularly from about 1,200° C. to about 1,800° C., and still more particularly from about 1,500° C. to about 1,700° C. Suitable sintering times range from about 5 minutes to about 100 minutes, and more particularly from about 8 minutes to about 15 minutes.

The sintering heating profile typically occurs in one or more steps. Preferably, sintering occurs in an atmosphere that limits the transfer of oxygen atoms to the tantalum. For example, sintering may occur in a reducing atmosphere, such as in a vacuum, inert gas, hydrogen, and the like. The reducing atmosphere may be at a pressure that ranges from about 10 Torr to about 2,000 Torr, more particularly from about 100 Torr to about 1,000 Torr, and still more particularly from about 100 Torr to about 930 Torr. Mixtures of hydrogen and other gases, for example, argon or nitrogen may also be employed as the sintering atmosphere.

Sintering causes the tantalum pellet to shrink due to the growth of metallurgical bonds between the tantalum particles. Because shrinkage generally increases the density of the pellet, lower press densities ("green") may be employed to achieve the desired target density. For example, the target density of the anode pellet after sintering typically ranges from about 5 grams per cubic centimeter (g/cm$^3$) to about 8 g/cm$^3$. Because of the shrinking phenomenon, however, the tantalum pellet need not be pressed to such high densities but may instead be pressed to densities of less than about 6.0 g/cm$^3$, and more particularly from about 4.5 g/cm$^3$ to about 5.5 g/cm$^3$.

The exemplary anodes 54, 58 and 60 contain a dielectric formed by anodically oxidizing ("anodizing") a sintered pellet so that a dielectric layer is formed over and within the tantalum forming the pellet. For example, the tantalum anodes 54, 58 and 60 may be anodized to form tantalum pentoxide (Ta$_2$O$_5$). Typically, anodization is performed by positioning the tantalum pellet in an anodizing electrolyte. Aqueous solvents (e.g., water) and/or non-aqueous solvents, for example, ethylene glycol may be employed in the anodizing electrolyte.

To enhance conductivity of the anodizing electrolyte, a compound may be used that is capable of dissociating in the solvent to form ions. Examples of such compounds include, for example, acids, such as those described below with respect to the working electrolyte. For example, phosphoric acid may constitute from about 0.01 wt. % to about 5 wt. %, particularly from about 0.05 wt. % to about 0.8 wt. %, and still more particularly from about 0.1 wt. % to about 0.5 wt. % of the anodizing electrolyte. If desired, blends of acids may also be employed.

During the anodizing process, a current is passed through the anodizing electrolyte to form the dielectric layer on the tantalum particles. The value of the formation voltage determines the thickness of the dielectric layer. For example, the power supply may be initially set at a galvanostatic mode until the required voltage is reached. Thereafter, the power supply may be switched to a potentiostatic mode to ensure that the desired dielectric thickness is formed over the entire surface of the tantalum pellet. Of course, other known anodizing methods may be employed, such as pulse or step potentiostatic methods.

To achieve a capacitor capable of operating at a relatively high voltage range, the voltage at which anodic oxidation occurs is relatively high. The anodizing voltage typically ranges from about 100 volts to about 500 volts, more particularly from about 200 volts to about 450 volts, and still more particularly from about 250 volts to about 430 volts. The temperature of the anodizing electrolyte ranges from about 10° C. to about 200° C., more particularly from about 20° C. to about 150° C., and still more particularly from about 30° C. to about 90° C. The resulting dielectric layer is formed on both the outer surface of the tantalum pellet and within pores inside the pellet.

U.S. Pat. No. 6,231,993 to Stephenson et al. describes an anodizing process where a tantalum pellet is formed by periodically holding the pellet at a constant voltage and allowing the current to decay over a period, or by turning the formation power supply off altogether during the anodization process. Either way provides an opportunity for heated anodizing electrolyte to diffuse from the anodized tantalum pellet. The '993 patent is assigned to the assignee of the present invention and incorporated herein by reference.

Figure 6:
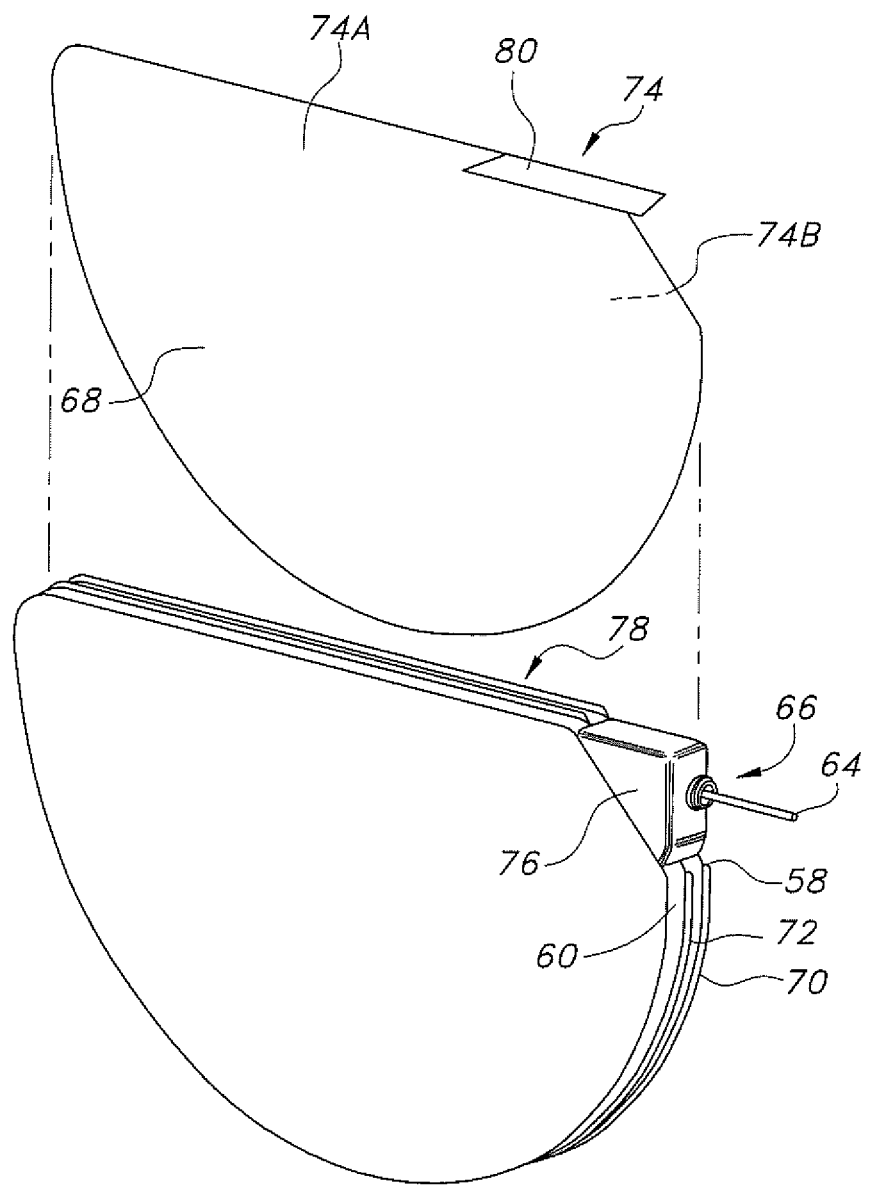
FIG. 6 is a perspective view of the anode assembly shown in FIG. 3 with an intermediate cathode current collector 74 being disposed between the pair of anodes 58 and 60.

The capacitor 10 further comprises separators of electrically insulative material that surround and envelop the anodes 54, 58 and 60. As shown in FIG. 2, a separator envelope 68 encloses the single anode 54. FIG. 6 shows a first separator envelope 70 encloses the first anode 58 and a second separator envelope 72 encloses the second anode 60 in the dual anode assembly. In that manner, the respective separators 68, 70 and 72 prevent an internal electrical short circuit between the anode and cathode materials in the assembled capacitor 10 and have a degree of porosity sufficient to allow flow therethrough of the working electrolyte during the electrochemical reaction of the capacitor.

Illustrative separator materials include woven and non-woven fabrics of polyolefinic fibers including polypropylene and polyethylene, or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials.

Suitable microporous films include a polyethylene membrane commercially available under the designation SOLUPOR®, (DMS Solutech); a polytetrafluoroethylene membrane commercially available under the designation ZITEX®, (Chemplast Inc.) or EXCELLERATOR®, (W. L. Gore and Associates); a polypropylene membrane commercially available under the designation CELGARD®, (Celgard LLC); and a membrane commercially available under the designation DEXIGLAS®, (C. H. Dexter, Div., Dexter Corp.). Cellulose based separators also typically used in capacitors are contemplated by the scope of the present invention. Depending on the electrolyte used, the separator can be treated to improve its wettability, for example with a surfactant, as is well known by those skilled in the art.

The cathode of capacitor 10 comprises a cathode material supported by and in contact with the inner surfaces of face walls of the casing members. In the casing 12 shown in FIG. 1, the cathode material is supported on the face walls 18 and 24 of the respective casing members 14 and 16. In the embodiment shown in FIG. 2, the cathode material is supported by and in contact with the inner surfaces of the face walls 38 and 46 of the casing members 32 and 34. In any event, the cathode material has a thickness of about a few hundred Angstroms to about 0.1 millimeters directly coated on the inner surfaces of the face walls of casing members, or the cathode material may be coated on a conductive substrate (not shown) in electrical contact with the inner surface of the face walls. With reference to the dual anode embodiment shown in FIGS. 3 and 6, cathode material 68 is also positioned intermediate the anodes 58 and 60, supported on the opposed first and second major faces 74A and 74B of a cathode current collector 74, which is preferably in the form of a foil. In that respect, the respective face walls 14, 16 (FIG. 1) and 38, 46 (FIG. 2) and the intermediate current collector 74 (FIG. 6) may be of an anodized-etched conductive material, or have a sintered active material with or without oxide contacted thereto, or be contacted with a double layer capacitive material, for example a finely divided carbonaceous material such as graphite or carbon or platinum black, or be contacted with a redox, pseudocapacitive or an under potential material, or an electroactive conducting polymer such as polyaniline, polypyrrole, polythiophene, and polyacetylene, and mixtures thereof.

According to one preferred aspect of the present capacitor 10, the redox or cathode material 68 includes an oxide of a metal, the nitride of the metal, the carbon nitride of the metal, and/or the carbide of the metal, the oxide, nitride, carbon nitride and carbide having pseudocapacitive properties. The metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead. Ruthenium oxide is a preferred cathode material 68 coated on the interior surfaces of the respective casing members 14, 16 (FIG. 1) and 38, 46 (FIG. 2) and on the intermediate current collector (FIG. 6) or a separate conductive substrate is electrically supported on the interior surfaces of the casing members.

FIG. 6 shows that although the wire 62 connecting the anode 58 and 60 in parallel is potted in a polymer block 76, the anodes are slightly separable due to the flexibility of the embedded wire at the junction of the polymer and the anode pellets themselves. The anodes 58 and 60 are sufficiently separable to allow the cathode current collector 74 to be inserted between them, as indicated by arrows 78. That way, the cathode current collector 74 is positioned between the opposed inner faces of the first and second anodes 58 and 60 with the first and second major faces 74A and 74B of the cathode current collector having the cathode material 68 supported thereon facing the anodes, thereby forming an anode-cathode assembly. A tab 80 that extends outwardly from the cathode current collector 74 is configured for tack welding to the inner surface of the surrounding side wall 20 of casing member 14. The tab 80 is bent approximately perpendicular to the faces 74A and 74B to position it for welding to side wall 20.

In a functioning capacitor 10, a working electrolyte is in electrical contact or communication with the cathode material 68 and the anodes 54, 58 and 60. The working electrolyte is a fluid that may soaked into the anodes 54, 58 and 60, or it may be added to the capacitor 10 through a fill port 82 (FIG. 1) at a later stage of production. Preferably, the fluidic electrolyte uniformly wets the dielectric on the tantalum anodes 54, 58 and 60.

Typically, the working electrolyte has an electrical conductivity of from about 0.01 Siemens per centimeter ("S/cm") to about 0.1 S/cm, more particularly from about 0.02 S/cm to about 15 S/cm, and still more particularly from about 0.02 S/cm to about 10 S/cm, determined at a temperature of about 25° C. using any known electric conductivity meter. The working electrolyte is generally in the form of a liquid, such as an aqueous or non-aqueous solution. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution).

The desired ionic conductivity may be achieved by selecting ionic compounds, for example, acids, bases, salts, and the like, within certain concentration ranges. In one embodiment, salts of weak organic acids may be effective in achieving the desired electrolyte conductivity. The cation of the salt may include monatomic cations, such as alkali metals (e.g., $Li^+$, $Na^+$, $K^+$, $Rb^+$, or $Cs^+$), alkaline earth metals, for example, $Be^{2+}$, $Mg^{2+}$, $Ca^{2+}$, $Sr^{2+}$ or $Ba^{2+}$, transition metals, for example, $Ag^+$, $Fe^{2+}$, $Fe^{3+}$, as well as polyatomic cations, such as $NH^4$. The monovalent ammonium ($NH_4^+$), sodium ($K^+$), and lithium ($Li^+$) are particularly suitable cations for use in the present capacitor. The organic acid used to form the anion of the salt may be "weak" in the sense that the acid typically has a first acid dissociation constant ($pK_{a1}$) of about 0 to about 11, more particularly about 1 to about 10, and still more particularly from about 2 to about 10, determined at about 23° C. Any suitable weak organic acid may be used, for example, a carboxylic acid, an acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc., and blends thereof. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40).

While the actual amounts may vary depending on the particular salt employed, the salt's solubility in the solvent or solvents used in the working electrolyte, and the presence of other components, such weak organic acid salts in the working electrolyte are in amounts that range from about 0.1 wt. % to about 25 wt. %, particularly from about 0.2 wt. % to about 20 wt. %, and more particularly from about 0.3 wt. % to about 15 wt. %, and still more particularly from about 0.5 wt. % to about 5 wt. %.

The working electrolyte is typically aqueous in that it contains an aqueous solvent, such as deionized water. For example, deionized water may constitute from about 20 wt. % to about 95 wt. %, more particularly from about 30 wt. % to about 90 wt. %, and still more particularly from about 40 wt. % to about 85 wt. % of the working electrolyte.

A secondary solvent may be employed to form a solvent mixture. Suitable secondary solvents include, for example, glycols (e.g., ethylene glycol, propylene glycol, butylene glycol, triethylene glycol, hexylene glycol, polyethylene glycols, ethoxydiglycol, dipropyleneglycol); glycol ethers (e.g., methyl glycol ether, ethyl glycol ether, isopropyl glycol ether); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane).

Such solvent mixtures typically contain water in an amount that ranges from about 40 wt. % to about 80 wt. %, more particularly from about 50 wt. % to about 75 wt. %, and still more particularly from about 55 wt. % to about 70 wt. %, and a secondary solvent in an amount that ranges from about 20 wt. % to about 60 wt. %, more particularly from about 25 wt. % to about 50 wt. %, and still more particularly from about 30 wt. % to about 45 wt. %. The secondary solvent or solvents may, for example, constitute from about 5 wt. % to about 45 wt. %, more particularly from about 10 wt. % to about 40 wt. %, and still more particularly from about 15 wt. % to about 35 wt. % of the working electrolyte.

If desired, the working electrolyte may be relatively neutral and have a pH of from about 4.5 to about 8.0, more particularly from about 5.0 to about 7.5, and still more particularly from about 5.5 to about 7.0. One or more pH adjusters, for example, acids or bases may be used to help achieve the desired pH. In one embodiment, an acid is used to lower the pH to the desired range. Suitable acids for this purpose include, for example, organic acids such as described above; inorganic acids, such as hydrochloric acid, nitric acid, sulfuric acid, phosphoric acid, polyphosphoric acid, boric acid, boronic acid, and mixtures thereof. Although the total concentration of the pH adjuster may vary, it is typically present in an amount that ranges from about 0.01 wt. % to about 10 wt. %, more particularly from about 0.05 wt. % to about 5 wt. %, and still more particularly from about 0.1 wt. % to about 2 wt. % of the working electrolyte.

The working electrolyte may also contain other components that help improve the electrical performance of the capacitor 10. For instance, a depolarizer may be employed in the working electrolyte to help inhibit the evolution of hydrogen gas at the cathode, which could otherwise cause the capacitor 10 to bulge and eventually fail. When used, the depolarizer typically constitutes from about 1 parts per million ("ppm") to about 500 ppm, more particularly from about 10 ppm to about 200 ppm, and still more particularly from about 20 ppm to about 150 ppm of the working electrolyte.

Suitable depolarizers include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroace tophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid. Particularly suitable nitroaromatic depolarizers for use in the present capacitor are nitrobenzoic acids, anhydrides or salts thereof, substituted with one or more alkyl groups (e.g., methyl, ethyl, propyl, butyl). Specific examples of such alkyl-substituted nitrobenzoic compounds include, for example, 2-methyl-3-nitrobenzoic acid, 2-methyl-6-nitrobenzoic acid, 3-methyl-2-nitrobenzoic acid, 3-methyl-4-nitrobenzoic acid, 3-methyl-6-nitrobenzoic acid, 4-methyl-3-nitrobenzoic acid, anhydrides or salts thereof.

Specific examples of suitable working electrolytes are described in U.S. Pat. Nos. 5,369,547 and 6,594,140, both to Evans et al., U.S. Pat. No. 6,219,222, now Reissue Pat. No. Re47,435 to Shah et al., and U.S. Pat. No. 6,687,117 to Liu et al. The Evans et al. patents are incorporated herein by reference. The Shah et al. and Liu et al. patents are assigned to the assignee of the present invention and incorporated herein by reference.

Referring back to FIG. 1, the feedthrough 66 electrically insolates the anode terminal wire 64 from the casing 12. The anode terminal wire 64 extends from inside the casing 12 to the outside thereof. A hole is provided in the surrounding sidewall 20 of the casing member 14 into which the feedthrough 66 is mounted. The feedthrough 66 may, for example, be a glass-to-metal seal ("GTMS") that contains a ferrule with an internal cylindrical bore of a constant inside diameter. An insulative glass provides a hermetic seal between the bore of the ferrule and anode terminal wire 64 passing therethrough.

After welding the feedthrough to the casing member 14 and then sealing the casing members 14, 16 together to form the casing 12 housing the anode and the cathode, the working electrolyte is introduced into the casing through the fill-port 82. Filling may be accomplished by placing the casing 12 in a vacuum chamber so that the fill-port 82 extends into a reservoir of the working electrolyte. When the chamber is evacuated, pressure is reduced inside the casing 12. When the vacuum is released, pressure inside the casing 12 re-equilibrates, and the working electrolyte is drawn through the fill-port 82 into the casing 12. The fill port 82 is then hermetically sealed, for example by welding a closure system into the fill port to complete manufacturing the capacitor 10.

Regardless of its configuration, the capacitor 10 of the present invention exhibits excellent electrical properties. For example, the capacitor may exhibit a high volumetric efficiency, such as from about 50,000 $\mu F*V/cm^3$ to about 300,000 $\mu F*V/cm^3$, more particularly from about 60,000 $\mu F*V/cm^3$ to about 200,000 $\mu F*V/cm^3$, and still more particularly, from about 80,000 $\mu F*V/cm^3$ to about 150,000 $\mu F*V/cm^3$, determined at a frequency of 120 Hz and at room temperature (e.g., 25° C.). Volumetric efficiency is determined by multiplying the formation voltage of an anode by its capacitance, and then dividing the product by the volume of the anode. For example, a formation voltage may be 360 volts for an anode having a capacitance of 785 µF, which results in an anode having 204,000 µF*V. If the anode occupies a volume of about 2.33 $cm^3$, this results in a volumetric efficiency of about 87,596 $\mu F*V/cm^3$. The anodes 54, 58 and 60 of the present invention are characterized as having been formed to a voltage that ranges from 270 volts to about 430 volts.

As previously discussed, U.S. Pat. No. 10,290,430 to Djebara et al. describes a tantalum powder having a specific charge that ranges from about 15,000 µF*V/g to about 45,000 µF*V/g. The prior art powder is useful as an anode in a wet tantalum electrolytic capacitor that can operate at a voltage that ranges from about 100 volts to about 300 volts. In contrast, the tantalum powder of the present invention has a lower specific charge that ranges from about 11,000 µF*V/g to about 14,000 µF*V/g. Even though the specific charge of the present tantalum powder is lower than that described in the prior art '430 patent, the energy density of the powder is higher because the voltage term is squared in the equation $E=\frac{1}{2}CV^2$. This results in a wet tantalum electrolytic capacitor that can operate at voltage that ranges from 250 volts to 390 volts, with the tantalum anodes having a breakdown voltage that ranges from about 250 volts to about 450 volts.

Thus, the capacitor 10 of the present invention exhibits a relatively high energy density that enables it to be suitable for use in high pulse applications. Energy density is generally determined according to the equation $E=\frac{1}{2}*CV^2$, where C is the capacitance in farads (F) and V is the working voltage of capacitor in volts (V). The capacitance may be measured using a capacitance meter (e.g., Quadtech 7400 Precision LCR meter with Kelvin Leads, 1-volt bias and 1-volt signal) at operating frequencies that range from 10 to 120 Hz (e.g., 120 Hz) at a temperature of 25° C.

For example, the capacitor 10 may exhibit an energy density of about 2.0 joules per cubic centimeter ($J/cm^3$), particularly about 3.0 $J/cm^3$, and more particularly from about 3.5 $J/cm^3$ to about 12.0 $J/cm^3$, and still more particularly from about 6.0 $J/cm^3$ to about 9.0 $J/cm^3$. The capacitor 10 may also exhibit a relatively high "breakdown voltage", defined as the voltage at which the capacitor fails, such as about 180 volts or more, more particularly 200 volts or more, and still more particularly from about 250 volts to about 450 volts.

The equivalent series resistance ("ESR"), which is the extent to which the capacitor 10 acts like a resistor when charging and discharging in an electronic circuit, is preferably less than about 15 ohms, particularly less than about 10 ohms, more particularly less than about 5 ohms, and still more particularly from about 0.5 ohms to about 4.5 ohms, as measured with a 1-volt bias and 1-volt signal at a frequency of 120 Hz.

In addition, the leakage current, which generally refers to the current flowing from one conductor to an adjacent conductor through an insulator, can be maintained at relatively low levels. For example, the numerical value of the normalized leakage current of the capacitor 10 of the present invention is less than about 10 nA/μF*V, more particularly less than about 5 nA/μF*V, and still more particularly less than about 2 nA/μF*V, where nA is nanoamps and μF*V is the product of the capacitance and the rated voltage. Leakage current may be measured holding the capacitor 10 at a certain rated voltage after a charging time of from about 60 to about 300 seconds and measuring current.

The electrolytic capacitor 10 of the present invention is useful in various applications, including but not limited to implantable medical devices, such as implantable defibrillators, subcutaneous implantable defibrillators, pacemakers, cardioverters, neural stimulators, drug administering devices, etc. In one embodiment, for example, the capacitor 10 may be employed in an implantable medical device configured to provide a therapeutic high voltage (e.g., between approximately 500 volts and approximately 850 volts, or, desirably, between approximately 600 Volts and approximately 900 volts) treatment for a patient. The medical device has a housing that is hermetically sealed and biologically inert. One or more leads are electrically coupled between the medical device and the patient's heart via a vein. Cardiac electrodes are provided to sense cardiac activity and/or provide a voltage to the heart. The medical device, for example the implantable cardioverter defibrillator ("ICD") also contains a capacitor bank that typically contains two or more capacitors 10 connected in series and coupled to a battery. The battery supplies energy to the capacitor bank. Due in part to high conductivity, the capacitor 10 of the present invention can achieve excellent electrical properties and thus is suitable for use in the capacitor bank of an ICD.

The present invention may be better understood by reference to the following example.

Test Procedures

Capacitance ("CAP"), equivalent series resistance ("ESR") and leakage current ("DCL") were tested in an aqueous neutral electrolyte at a temperature of 37° C.±0.5° C.

Capacitance ("CAP")

Capacitance was measured using a Quadtech 7400 Precision LCR meter with Kelvin Leads with 1-volt DC bias and a 0.5-volt peak to peak sinusoidal signal. The operating frequency was 120 Hz.

Equivalent Series Resistance ("ESR")

Equivalence series resistance was measured using a QUADTECH 7400 Precision LCR meter with Kelvin Leads 1-volt DC bias and a 0.5-volt peak to peak sinusoidal signal. The operating frequency was 120 Hz.

Leakage Current ("DCL")

Leakage current was determined by charging to 250V for 300 seconds without any resistor in series.

Example

Anodes were formed from a nodular, magnesium-reduced tantalum powder (H.C. Starck, now Taniobis GmbH). The powder was pressed to 5.5 g/cm$^3$ density. The tantalum pellets were vacuum sintered at 1,500° C. for 20 minutes. Upon sintering, the pellets were anodized in a solution (see table below) containing PEG/water or EG/water with phosphoric acid at a temperature of 40° C. and a conductivity of 1 mS/cm. The anodes were then joined together with two cathodes prepared from ruthenium oxide coated titanium sheets (0.1 mm thick) separated with microporous separator material. The resulting capacitors were then tested as described above. The results are set forth below.

Initial Test Results and Discussion

Figure 7:
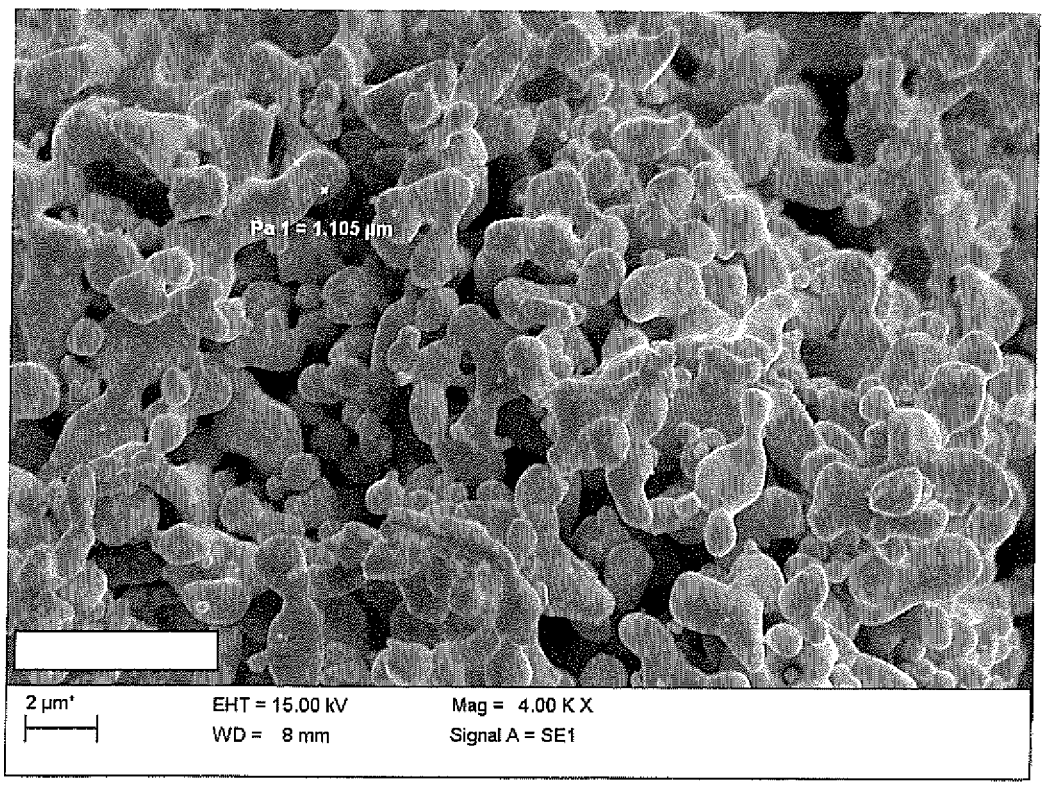
FIG. 7 is a photograph of a tantalum powder according to the present invention at 4,000× magnification.
Figure 8:
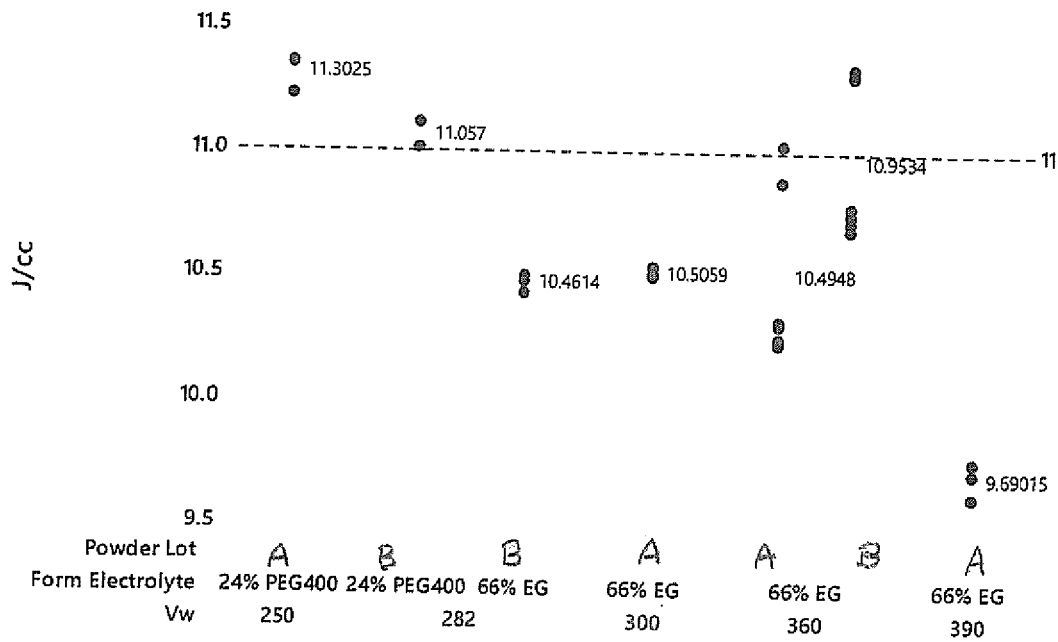
FIG. 8 is a graph of the energy density of tantalum powder lots A and B according to the example described herein.
Figure 9:
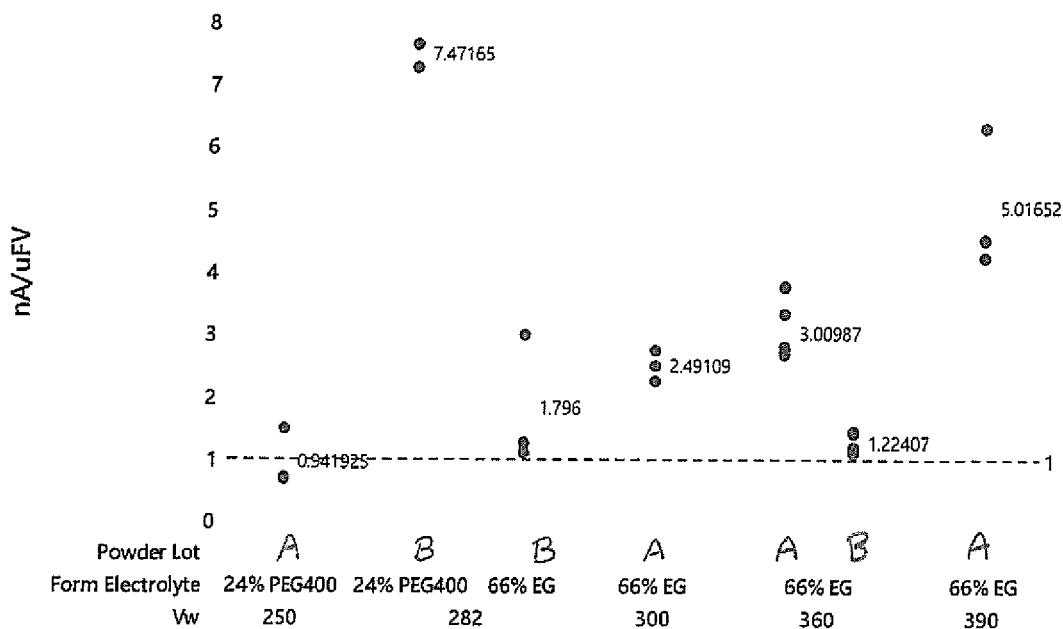
FIG. 9 is a graph of the leakage current (DCL) of various tantalum power lots A and B according to the example described herein.
Figure 10:
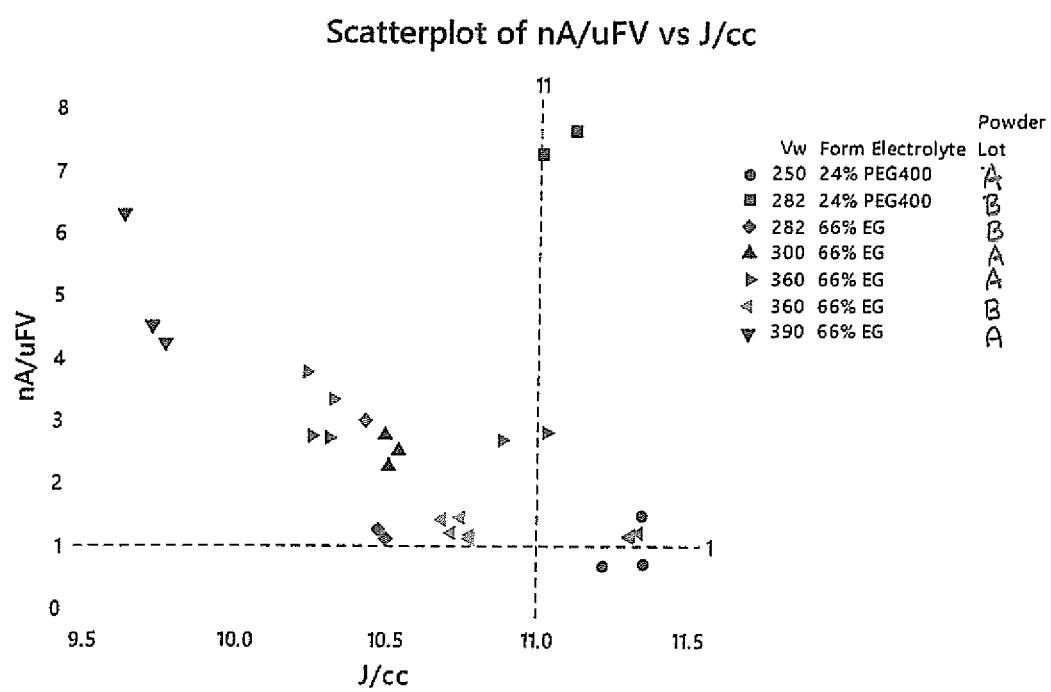
FIG. 10 is a graph plotting DCL vs. J/cc for two samples of tantalum powder lots A and B according to the example described herein.

Anodes were formed and tested at 390V, 360V, 300V, 282V and 250V for the received lots. The table below summarizes the overall results and is plotted on FIGS. 7, 8 and 9. The energy variation in the 360V results for FIG. 4 are related to changes in anode sintering conditions.

For the tantalum material of the present invention, the target anodic energy density is approximately 11 J/cc, and the DCL should be less than 1 nA/uFV.

Summary of Electrical Test Results

| Powder Lot | # Anodes | Form Voltage | Form Electrolyte | Test Voltage | Form Failures | AVG J/cc | AVG nA/μFV |
|---|---|---|---|---|---|---|---|
| A | 4 | 270 | 24% PEG400 | 250 | 1 | 11.3 | 0.94 |
| A | 3 | 428 | 66% EG | 390 | 0 | 9.69 | 5.02 |
| A | 2 | 390 | 66% EG | 360 | 0 | 10.95 | 2.75 |
| B | 5 | 390 | 66% EG | 360 | 0 | 10.74 | 1.26 |
| A | 5 | 390 | 66% EG | 360 | 1 | 10.27 | 3.14 |
| A | 3 | 330 | 24% PEG400 | 300 | 3 | NA | NA |
| A | 3 | 330 | 55% PEG400 | 300 | 3 | NA | NA |
| A | 3 | 330 | 66% EG | 300 | 0 | 10.51 | 2.49 |
| B | 4 | 310 | 24% PEG400 | 282 | 2 | 11.06 | 7.47 |
| B | 3 | 310 | 66% EG | 282 | 0 | 10.46 | 1.8 |
| B | 3 | 390 | 66% EG | 360 | 0 | 11.31 | 1.16 |

The nodular tantalum powder achieved a relatively high capacitance and low DCL. Using the capacitance values obtained and assuming an operating voltage, energy density ($E=0.5*CV^2$) indicated the nodular tantalum powder also had a significantly higher energy density.

Although several embodiments of the present invention have been described in detail, that is for purposes of illustration. Various modifications of each embodiment may be made without departing from the scope of the present invention. Accordingly, the present invention is not to be limited, except as by the appended claims.

What is claimed is:

1. An electrolytic capacitor for use in an implantable medical device, the electrolytic capacitor comprising:
   a) a casing;
   b) at least one tantalum anode housed in the casing, the at least one tantalum anode comprising an anodically oxidized pellet formed from a pressed and sintered tantalum powder of agglomerated tantalum particles, wherein the at least one tantalum anode is characterized as having been formed to a voltage that ranges from 270 volts to about 430 volts, and wherein the tantalum powder has:
      i) tantalum particles with an aspect ratio of about 1 to about 2;
      ii) tantalum particles with sinter necks having a thickness that ranges from about 200 nanometers to about 1,100 nanometers;
      iii) a specific charge that ranges from about 11,000 µF*V/g to about 14,000 µF*V/g, and
      iv) wherein the at least one tantalum anode has a breakdown voltage that ranges from about 300 volts to about 450 volts;
   c) a lead wire that extends from the at least one tantalum anode to outside the casing, the lead wire being electrically isolated from the casing;
   d) a cathode comprising a cathode material coated on at least one inner surface of the casing or coated on a conductive substrate electrically connected to the casing, the cathode material facing the at least one tantalum anode; and
   e) a fluidic working electrolyte contained in the casing in contact with the at least one tantalum anode and the cathode.

2. The capacitor of claim 1, wherein the at least one tantalum anode has a breakdown voltage that ranges from about 360 volts to about 390 volts.

3. The electrolytic capacitor of claim 1, wherein the sinter necks have a thickness that ranges from about 500 nanometers to about 800 nanometers.

4. The electrolytic capacitor of claim 1, wherein the tantalum powder has an energy density that ranges from about 2.0 J/cm$^3$ to about 11.0 J/cm$^3$.

5. The electrolytic capacitor of claim 1, wherein in addition to the at least one tantalum anode, the casing houses at least a second tantalum anode, and wherein the cathode material coated on the conductive substrate is positioned between the at least one tantalum anode and at least the second tantalum anode.

6. The electrolytic capacitor of claim 1, wherein the tantalum powder is formed by reacting an oxide of tantalum with a reducing agent that contains magnesium, strontium, barium, cesium, calcium, aluminum, and a combination thereof.

7. The electrolytic capacitor of claim 1, wherein the tantalum powder has a specific surface area that ranges from about 0.4 m$^2$/g to about 1 m$^2$/g.

8. The electrolytic capacitor of claim 1, wherein the tantalum powder has no more than about 50 ppm of an alkali metal.

9. The electrolytic capacitor of claim 1, wherein the tantalum powder is nodular or angular.

10. The electrolytic capacitor of claim 1, wherein the at least one tantalum anode is comprised of primary particles of tantalum have a median size that ranges from about 10 nanometers to about 500 nanometers.

11. The electrolytic capacitor of claim 1, wherein the at least one tantalum anode has a thickness that ranges from about 0.1 millimeters to about 3.5 millimeters, and a width that ranges from about 2 to about 25 millimeters.

12. The electrolytic capacitor of claim 1, wherein the casing is selected from the group of titanium, tantalum, nickel, molybdenum, niobium, cobalt, stainless steel, tungsten, platinum, palladium, silver, copper, chromium, vanadium, aluminum, zirconium, hafnium, zinc, iron, and mixtures and alloys thereof.

13. The electrolytic capacitor of claim 1, wherein the cathode material is selected from an anodized-etched conductive material, a sintered active material with or without oxide contacted thereto, a double layer capacitive material, a finely divided carbonaceous material, graphite, carbon, platinum black, a redox, pseudocapacitive, an under potential material, an electroactive conducting polymer, polyaniline, polypyrrole, polythiophene, polyacetylene.

14. The electrolytic capacitor of claim 1, wherein the cathode material is selected from an oxide of a metal, a nitride of the metal, a carbon nitride of the metal, and a carbide of the metal, the metal being selected from the group of ruthenium, cobalt, manganese, molybdenum, tungsten, tantalum, iron, niobium, iridium, titanium, zirconium, hafnium, rhodium, vanadium, osmium, palladium, platinum, nickel, and lead.

15. The electrolytic capacitor of claim 1, wherein the working electrolyte has a pH that ranges from about 5.0 to about 7.5.

16. The electrolytic capacitor of claim 1, wherein a separator is positioned between the at least one tantalum anode and the cathode.

17. The electrolytic capacitor of claim 1, wherein the casing comprises a first casing member having a face wall meeting a surrounding sidewall that extends to an edge, and a second plate-shaped casing member that is sealed to the edge of the surrounding sidewall of the first casing member.

18. The electrolytic capacitor of claim 1, wherein the casing comprises mating clamshell-type casing member that are hermetically sealed together.

19. An implantable medical device comprising the electrolytic capacitor of claim 1.

20. An electrolytic capacitor for use in an implantable medical device, the electrolytic capacitor comprising:
   a) a casing;
   b) at least one tantalum anode housed in the casing, the at least one tantalum anode comprising an anodically oxidized pellet formed from a pressed and sintered tantalum powder of agglomerated tantalum particles, wherein the at least one tantalum anode is characterized as having been formed to a voltage that ranges from 270 volts to about 430 volts, and wherein the tantalum powder has:
      i) tantalum particles with an aspect ratio of about 1 to about 2;
      ii) tantalum particles with sinter necks having a thickness that ranges from about 200 nanometers to about 1,100 nanometers;

iii) a specific charge that ranges from about 11,000 µF*V/g to about 14,000 µF*V/g,
iv) wherein the at least one tantalum anode has a breakdown voltage that ranges from about 300 volts to about 450 volts;
c) a lead wire that extends from the at least one tantalum anode to outside the casing, the lead wire being electrically isolated from the casing;
d) a cathode comprising ruthenium oxide coated on at least one inner surface of the casing or coated on a conductive substrate electrically connected to the casing, the ruthenium oxide facing the at least one tantalum anode; and
e) a fluidic working electrolyte contained in the casing in contact with the at least one tantalum anode and the cathode.

21. The electrolytic capacitor of claim 20, wherein the at least one tantalum anode has a breakdown voltage that ranges from about 360 volts to about 390 volts.

22. The electrolytic capacitor of claim 20, wherein the sinter necks have a thickness that ranges from about 500 nanometers to about 800 nanometers.

* * * * *